US012758296B2

(12) United States Patent
Zhang et al.

(10) Patent No.: US 12,758,296 B2
(45) Date of Patent: Oct. 13, 2026

(54) APPARATUSES AND METHODS FOR COMBINATION RADIO FREQUENCY AND CRYO ABLATION TREATMENTS

(71) Applicant: Varian Medical Systems, Inc., Palo Alto, CA (US)

(72) Inventors: Hongxuan Zhang, Austin, TX (US); Vineel Vallapureddy, Plymouth, MN (US)

(73) Assignee: Varian Medical Systems, Inc., Palo Alto, CA (US)

( * ) Notice: Subject to any disclaimer, the term of this patent is extended or adjusted under 35 U.S.C. 154(b) by 736 days.

(21) Appl. No.: 17/845,597

(22) Filed: Jun. 21, 2022

(65) Prior Publication Data

US 2023/0404647 A1 Dec. 21, 2023

(51) Int. Cl.
*A61B 18/14* (2006.01)
*A61B 18/02* (2006.01)
*A61B 18/00* (2006.01)

(52) U.S. Cl.
CPC .............. *A61B 18/14* (2013.01); *A61B 18/02* (2013.01); *A61B 2018/00577* (2013.01); *A61B 2018/00589* (2013.01); *A61B 2018/0256* (2013.01)

(58) Field of Classification Search
CPC ..... A61B 18/02; A61B 18/14; A61B 18/1815; A61B 2018/00011; A61B 2018/00023; A61B 2018/00577; A61B 2018/00589; A61B 2018/0212; A61B 2018/0256; A61B 2018/1467
See application file for complete search history.

(56) References Cited

U.S. PATENT DOCUMENTS 6,540,740 B2 * 4/2003 Lehmann ............... A61B 18/02 606/22
7,097,641 B1 * 8/2006 Arless .................... A61B 18/02 607/101
8,998,892 B2 * 4/2015 Winkler ............ A61B 18/1482 606/41
9,717,552 B2 * 8/2017 Cosman ................. A61B 18/16
9,918,772 B2 * 3/2018 Fischer .................. A61B 18/02
2004/0116917 A1 6/2004 Lentz
2004/0158237 A1 * 8/2004 Abboud ................. A61B 18/02 606/21
2004/0215178 A1 * 10/2004 Maurice ................. A61B 18/02 606/22
2005/0038422 A1 2/2005 Maurice
2010/0137857 A1 6/2010 Shroff et al.
(Continued)

FOREIGN PATENT DOCUMENTS

WO 2023249931 A1 12/2023
WO 2023249932 A1 12/2023

OTHER PUBLICATIONS

International Search Report and Written Opinion for PCT/US2023/025708 issued Sep. 20, 2023, 17 pages.

*Primary Examiner* — Michael F Peffley
(74) *Attorney, Agent, or Firm* — Morgan, Lewis & Bockius LLP; Manita Rawat

(57) ABSTRACT

A probe for performing an ablation treatment includes a shell defining an outer surface, a cooling path comprising an inflow path and a return path for a cryogen, and at least one radio frequency (RF) emitter. The probe is used to provide combination radio frequency (RF) and cryo treatments during a common procedure.

19 Claims, 7 Drawing Sheets

(56) References Cited

U.S. PATENT DOCUMENTS

| | | | | |
|---|---|---|---|---|
| 2012/0239019 | A1* | 9/2012 | Asconeguy ........ | A61B 18/1492 606/41 |
| 2012/0265186 | A1* | 10/2012 | Burger ............. | A61M 25/0138 606/41 |
| 2012/0265189 | A1* | 10/2012 | Davis ..................... | A61B 18/02 606/22 |
| 2012/0316552 | A1 | 12/2012 | Mayse et al. | |
| 2013/0324987 | A1 | 12/2013 | Leung et al. | |
| 2014/0316398 | A1* | 10/2014 | Kelly ..................... | A61B 18/02 606/24 |
| 2015/0045675 | A1* | 2/2015 | Chernomorsky .. | A61B 18/1477 606/41 |
| 2016/0331459 | A1 | 11/2016 | Townley et al. | |
| 2019/0365451 | A1 | 12/2019 | Jung, Jr. | |
| 2020/0030024 | A1 | 1/2020 | Rao et al. | |
| 2022/0133381 | A1 | 5/2022 | Prologo et al. | |
| 2023/0371997 | A1* | 11/2023 | Zhang .................... | A61B 18/02 |

* cited by examiner

APPARATUSES AND METHODS FOR COMBINATION RADIO FREQUENCY AND CRYO ABLATION TREATMENTS

FIELD

The present disclosure relates to apparatuses and methods for combination radio frequency (RF) and cryo ablation treatments. More particularly, the present disclosure relates to apparatuses and methods that may include and/or allow both RF and cryo cycles in ablation treatments.

BACKGROUND

This section provides background information related to the present disclosure which is not necessarily prior art.

Systems and methods for providing ablation treatments generally include the introduction of a probe at or near a target tissue in a patient. The target tissue may be an abnormal or undesirable tissue such as a tumor. The ablation treatment is performed to destroy the target tissue. In addition to destroying the target tissue, it is desirable to minimize damage or harm to healthy tissues that may be located near to the target tissue.

One type of ablation treatment is a cryoablation treatment. Cryoablation treatments may include cryoablation probes that are introduced at or near the target tissue in the patient. A cryoablation system may include an extremely cold cryogen (liquid, gas, or mixed phase) that may be passed through the probe in thermal contact with the target tissue. Heat from the tissue passes from the tissue, through the probe, and into the cryogen that removes heat from the targeted tissue. This removal of heat causes tissue to freeze, resulting in the destruction of the targeted tissue. When the tissue freezes, ice forms typically in an iceball. The iceball may be in the form a sphere, ellipsoid or other shape. It is desirable to perform cryoablation treatments such that the target tissue is completely frozen and that the freezing of surrounding tissues and/or body structures is minimized.

In other treatments, radio frequency (RF) energy can be used to ablate a target tissue and/or provide pain relief. A probe may be inserted at or near a target tissue in a patient during such treatments. The probe may emit or deliver radio frequency energy to the target tissue. In some examples, the radio frequency energy can heat the target tissue to an elevated temperature that may destroy the tissue. In other examples, the radio frequency energy may be delivered to provide pain relief to an affected region or target tissue.

Traditional or existing systems and methods suffer from various drawbacks. Some of these drawbacks may result from the extreme temperatures that are used to produce the iceballs during the cryoablation freezing cycles or the elevated temperatures used in RF ablation treatments. For example, it can be difficult to bring tissue temperatures back to more moderate temperatures following the freezing cycle. The time required to heat tissue and/or bring tissue to moderate temperatures can be longer than may be desirable. In other examples, the tissue may dessicate during RF treatments that results in a reduction of the effectiveness of the treatment. As such, treatment times can be longer than desired and may require subsequent procedures to be performed in additional treatment sessions rather than in a single treatment. There exists a need, therefore, for improved ablation systems and methods that allow for more effective treatments.

SUMMARY

This section provides a general summary of the disclosure, and is not a comprehensive disclosure of its full scope or all of its features.

In various embodiments of the present disclosure, apparatuses and methods for performing ablation treatments and radio frequency (RF) treatments are provided. The apparatuses and methods may include improvements directed to combination radio frequency (RF) and cryo treatments that may include heating and cooling cycles performed by a single probe. Such a combination RF-cryo probe may be part of a combination RF-cryo ablation system that can be used to address several shortcomings of existing and traditional ablation treatments.

In some embodiments of the present disclosure, a probe for performing an ablation treatment is provided. The combination RF-cryo probe may include a shell defining an outer surface and a cooling path comprising an inflow path and a return path each positioned radially inward of the shell, the cooling path configured to couple to a cryogen source. The probe may also include at least one radio frequency (RF) emitter configured to couple to a radio frequency (RF) source.

In one aspect, the cooling path may include a supply conduit, the inner surface of the supply conduit defining the inflow path, and the outer surface of the supply conduit and an inner surface of the shell defining the outflow path.

In another aspect, the cooling path may be configured to move liquid or gaseous nitrogen through the probe.

In another aspect, the at least one radio frequency (RF) emitter comprises a plurality of RF electrodes and the plurality of electrodes may be positioned on the shell.

In another aspect, the at least one radio frequency (RF) emitter may include a first RF electrode positioned at a first axial location relative to a distal end of the probe, and a second RF electrode positioned at a second axial location relative to a distal end of the probe.

In another aspect, the at least one radio frequency (RF) emitter may include a first RF electrode and a second RF electrode are each positioned at the same axial location on a shell of the probe. The first RF electrode may be positioned at a different circumferential position than the second RF electrode.

In another aspect, the at least one radio frequency (RF) emitter comprises a microwave antenna.

In some embodiments in accordance with the present disclosure a combination RF-cryo system is provided. The system may include a combination RF-cryo probe and a RF-cryo controller configured to control operating characteristics of the cryogen and characteristics of a radio frequency signal provided to the at least one radio frequency (RF) emitter.

In one aspect, the RF-cryo controller may include at least one RF-cryo computing device and a data bus.

In another aspect, the RF-cryo controller is positioned in a housing comprising one or more connectors for connection of the probe.

In some embodiments of the present disclosure a method performing an ablation treatment is provided. The method may include cooling a target tissue by moving a cryogen through a probe and heating the target tissue emitting radio frequency (RF) energy from a radio frequency (RF) emitter in the probe.

In another aspect, the steps of cooling the target tissue and heating the target tissue are performed during a common treatment.

In another aspect, the step of cooling the target tissue comprises forming an iceball at the target tissue.

In another aspect, the cryogen may include liquid or gaseous nitrogen.

In another aspect, the radio frequency (RF) emitter may include an RF electrode.

In another aspect, the radio frequency (RF) emitter includes a microwave antenna.

In another aspect, the step of heating the target tissue may include performing a coagulation treatment.

In another aspect, the step of heating the target tissue may include denaturing proteins at or near the target tissue.

In another aspect, the step of heating the target tissue may include ablating the target tissue.

In another aspect, the method may also include adding cement to a body structure when the temperature of the body structure is greater than a predetermined temperature, and wherein the method is performed during a common treatment.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
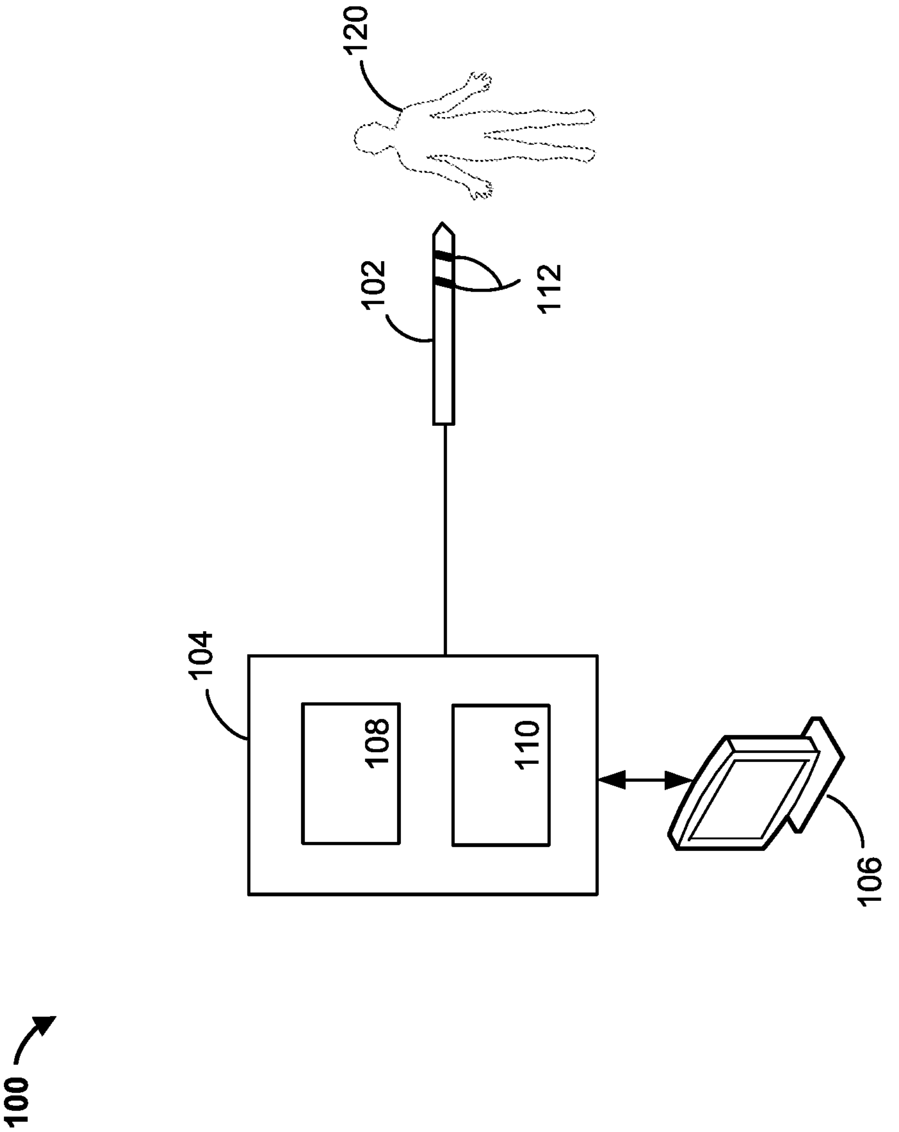
FIG. 1 is a diagram illustrating an example RF-Cryo ablation system in accordance with some embodiments of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

In some embodiments of the present disclosure, a combination RF-cryo ablation system is provided. The combination RF-cryo ablation system may allow both radio frequency (RF) treatments and cryogen treatments to be performed using a common probe. The probe may include, for example, an RF emitter such as a RF electrode and/or a microwave antenna. The probe may also include a cryogen flow path that moves a cryogen (e.g., liquid, gaseous, or a combination of liquid nitrogen) through the probe. Such a probe can be used, for example, to perform heating and freezing cycles during treatment that may be used for ablation of a target tissue and/or for pain relief. The systems and methods of the present disclosure provide improvements over existing systems by allowing for both modes of operation using a common probe. Such systems and methods provide various improvements that include the ability to perform treatments in lower treatment times than existing or conventional systems and methods. The systems and methods of the present disclosure can also improve the effectiveness of treatments and reduce harm to healthy tissues as will be further described below. Still further, the systems and methods of the present disclosure can allow more extensive treatments to be performed during a single treatment rather than having to perform multiple treatments and subject a patient to multiple medical procedures.

In one example treatment, the systems and methods of the present disclosure may be used to eliminate a need or reduce the likelihood that a subsequent follow-up treatment needs to be performed following a cryoablation treatment. In some cryoablation treatments, an iceball may be formed using a cryoablation probe at a target tissue (e.g., a tumor, lesion, or other abnormal tissue). If the target tissue is located at or near a bone or other support structure in a body of a patient, the structural integrity of the bone or support structure can be compromised if it is subjected to the low temperatures of the cryo treatment. Without further treatment, the bone or support structure may fail. A cement or other repair substance may be applied to the bone or support structure to address this condition. Such application of the cement or other repair substance is typically applied in a follow-up procedure following the cryo treatment because the tissues at or near the target tissue and iceball that is formed can take a significant amount of time to return to normal body temperatures.

The combination RF-cryo systems and probes of the present disclosure can be used in such a circumstance to improve the speed at which the target tissue and surrounding tissues are returned to normal body temperatures. For example, the RF functionality of the probes of the present disclosure may be used to heat the target tissue and surrounding body structures following a freezing cycle using the cryo functionality of the probe. The RF functionality can return a bone or other body structure at or near the site of the iceball to a temperature at which the cement or other repair substance can be applied during the same treatment session. In this manner, the patient does not need to undergo a follow-up treatment for the repair of the bone or body structure. Such improvement can reduce the need for multiple treatments and can improve the likelihood of a success treatment without undesirable harm to healthy tissues of the patient.

In another example circumstance, an ablation treatment may be performed in which a probe is inserted at or near a target tissue. The ablation treatment may cause bleeding to occur in the target tissue and/or in the surrounding tissue. The RF functionality of the systems and probes of the present disclosure can be used to heat the tissue at a bleeding site to induce coagulation and reduce or stop the bleeding condition. This functionality is an improvement over existing systems and methods. In many existing or traditional systems and methods, particularly with cryoablation systems and probes, the coagulation treatments are not possible or are not effective. The systems and methods of the present disclosure can use RF energy to more quickly heat and coagulate bleeding conditions that may occur than existing systems and methods. Such improvement can improve the effectiveness of treatments and reduce undesirable bleeding conditions that may occur.

In yet another example circumstance, a probe that is inserted at or near a target tissue may need to be repositioned. For example, during a cryoablation treatment, the probe may be inserted at or near the target tissue. If the needle/probe is not positioned in the desired location (as may be confirmed using imaging techniques), the probe may be moved or otherwise repositioned to the desired location. When the probe is removed and/or repositioned, the tissue into which probe was positioned may become contaminated. To prevent contamination and/or to reduce a likelihood of contamination, the RF functionality of the systems and probes of the present disclosure can be used to heat the tissue and denature proteins in the tissue. This functionality is not possible using existing systems and traditional cryoablation treatment methods.

In another example circumstance, multiple probes may used for a single cryoablation treatment. The multiple probes may be used to form an iceball of a predetermined size and/or shape at a target tissue. At the conclusion of the freezing cycle, the probes then need to be extracted from the patient. The removal of the probes can be difficult due to the existence of the ice at the target tissue. In such instances, the RF functionality of the systems and probes of the present disclosure can be used to heat the probes and/or the surrounding tissue to allow the probes to be removed. The RF functionality of the probes of the present disclosure can heat the ice at a more rapid rate than existing or traditional systems and methods. This, in turn, can reduce the length of an ablation treatment which is typically desirable to minimize the overall length of an ablation procedure.

In yet another example, an RF ablation procedure may be used to destroy a target tissue. The RF emitter (e.g., RF electrode or microwave antenna) may be used to elevate the temperature of the target tissue to predetermined temperature level that destroys the tissue. As the temperature of the tissue is elevated, the tissue may dessicate. This condition may change the conductivity or other properties of the tissue that causes a reduction in the rate at which the temperature of the tissue is elevated. Thus, the desiccation of tissue during RF ablation may cause more power to be required and/or the length of time of the RF ablation heating cycle to increase. In some examples in accordance with the present disclosure, the combination RF-cryo systems and probes can be used first in a cryo mode of operation to produce ice at the target tissue. The systems and probes can then be used in a RF mode of operation to rapidly elevate the temperature of the target tissue. In such methods, the amount of desiccation that occurs at the tissue can be reduced. Thus, the RF ablation can be performed with less power and/or in a reduced period of time.

The above examples briefly describe possible circumstances and related methods that may be used that are improvements over existing systems and methods. It should be appreciated that the combination RF-cryo systems and probes of the present disclosure can also be used in other circumstances to perform other methods and treatments.

Turning now to FIG. 1, and example combination RF-cryo system 100 is shown. The combination RF-cryo system 100 may include a RF-cryo controller 104 that is coupled to a RF-cryo computing device 106 and to a RF-cryo probe 102. The combination RF-cryo system 100 may be configured to operate in an RF mode and in a cryo mode to provide ablation and other treatments to a patient 120. The RF-cryo controller 104 may include a cryo delivery system 108 and a RF delivery system 110 that will be further described.

The cryo delivery system 108 can deliver a cryogen to the probe 102. The cryogen can remove heat from the probe and from tissue that may be located near the probe 102 when the probe 102 is positioned in a desired location in the patient 120. The probe 102 may be positioned, for example, at or near a target tissue such as a tumor, lesion, or the abnormal tissue. The cryo delivery system 108 can cause an iceball (of various suitable shapes and sizes) to be produced at a distal end of the probe 102 that destroys the target tissue. The cryogen may be various suitable fluids. In one example, the cryo delivery system 108 is configured to deliver liquid and/or gaseous nitrogen to the probe 102.

The RF delivery system 110 can be configured to deliver RF energy to the probe 102. The RF delivery system 110 can deliver an electrical current, for example, to the probe 102 that can be transferred to the surrounding tissue of the patient 120 via one or more RF electrodes 112. The RF electrodes 112 can be positioned at or near a distal end of the probe 102. In this manner, the RF energy can be transferred to the target tissue and, in turn, heat the tissue at the distal end of the probe 102. The heat can be produced using various duty cycles and/or via various power profiles to elevate the temperature of the tissue to destroy the tissue, coagulate a bleeding condition, and/or return the turn the tissue a normal body temperature as may be desired.

The probe 102, in the example shown, includes one or more RF electrodes 112. In other examples, the probe 102 may include a microwave antenna. The antenna may be positioned at the distal end of the probe 102. The RF delivery system 110 can deliver a current to the antenna (via a coaxial cable in the probe, for example) to cause microwaves to be emitted. The microwaves, in turn, can heat the tissue at or near the distal end of the probe 102 to destroy tissue, coagulate a bleeding condition, and/or return the tissue to a normal body temperature. In still other examples, the RF electrodes and/or the microwave antenna may be used to treat a pain condition in the patient via delivery of the RF energy. In the present disclosure, the term RF emitter is used to describe various structures that use RF energy to heat tissue at the distal end of the probe 102. Such various structures may include RF electrodes, microwave antennas and the like.

The combination RF-cryo system 100 may also include the RF-cryo computing device 106 that is coupled to the RF-cryo controller 104. While the RF-cryo controller 104 and the RF-cryo computing device are shown as separate elements in FIG. 1, it should be appreciated that these elements (and other elements) may be combined into single structures or be further separated from that shown and described.

The RF-cryo computing device 106 may be various suitable processing devices such as a computer, server, laptop, tablet, workstation, circuit, or the like to provide the functionality described. The RF-cryo computing device 106 may also include a display and/or other input-output devices to allow a user to interact, control, view, and otherwise configure the operation of the combination RF-cryo system 100.

Figure 2:
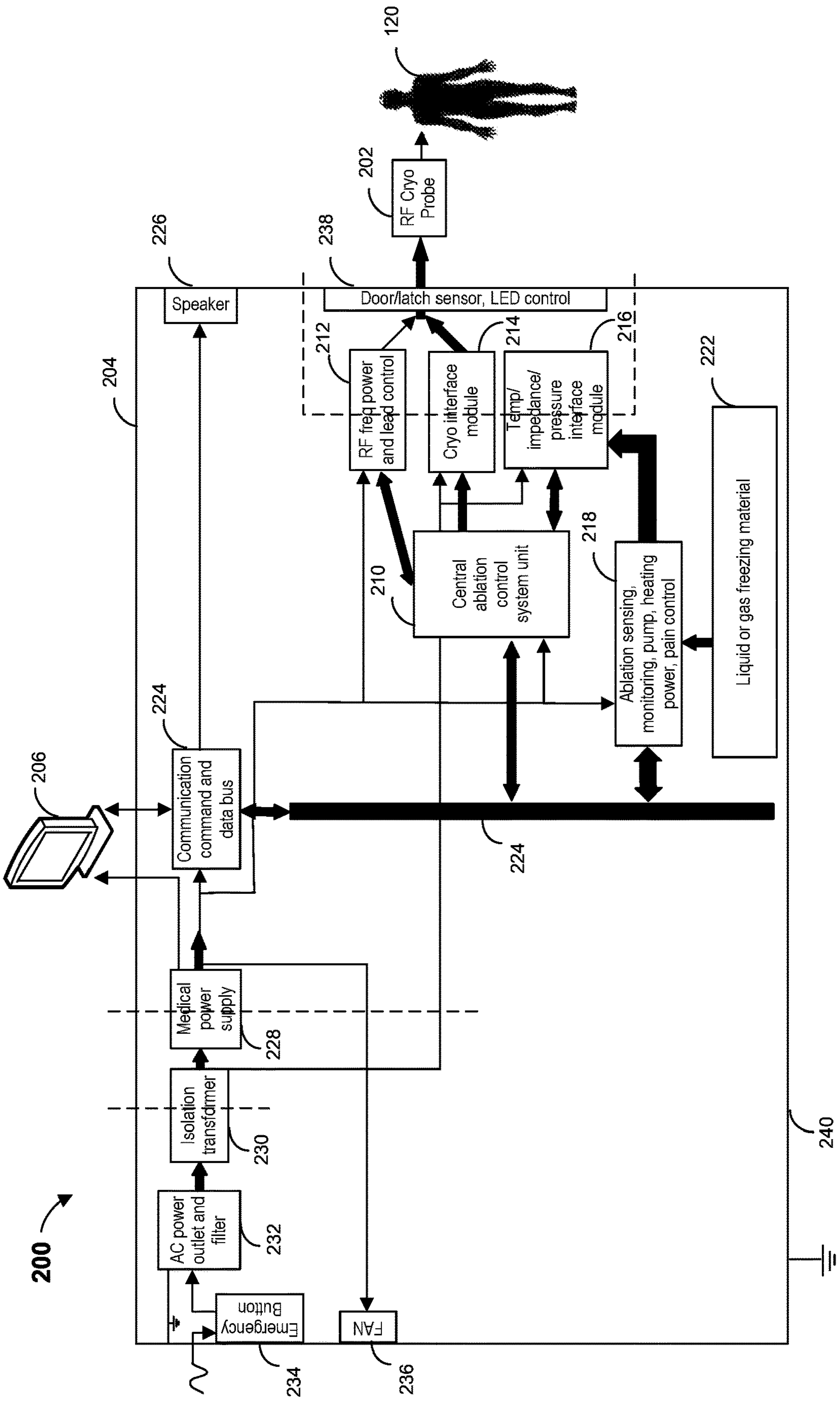
FIG. 2 is a diagram illustrating aspects of an example RF-Cryo ablation unit in accordance with some embodiments of the present disclosure.

Another example combination RF-cryo system 200 is shown in FIG. 2. The RF-cryo system 200 is similar to the system 100 previously described and can operate in a similar manner to provide both cryo freezing cycles and RF heating cycles via the RF-cryo probe 202. The RF-cryo system 200 can include a RF-cryo controller 204 that can couple to a RF-cryo computing device 206 and to a RF-cryo probe 202. The RF-cryo controller 204 can be configured as a portable piece of equipment contained in a housing 240. The chamber 240 can include walls to house the various internal elements and include ports, connectors, plugs, cords, conduits and the like to connect to the RF-cryo computing device 206 and the RF-cryo probe 202.

As shown, the RF-cryo controller can couple to the RF-cryo computing device 206 via both the medical power supply 228 and the data bus 224. The medical power supply 228 can provide power to the various elements of the RF-cryo controller 204 and can be coupled to an external power source via an isolation transformer 230 and the power outlet and filter 232. The housing 240 can include an emergency button 234 that can allow an operator to interrupt power to the RF-cryo controller 204. A fan 236 may also be positioned in the housing 240 to provide air flow and/or cooling to the electrical components inside the RF-cryo controller 204.

The data bus 224 can extend in the housing 240 and be coupled to various elements that control and obtain data and information for use during a treatment. As shown, the data bus 224 can be coupled to a central ablation control system unit 210, and an ablation sensing, monitoring, pump, heating power and pain control unit 218. The central ablation control system unit 210 can, in turn, be coupled to a RF power and lead control 212, a cryo interface module, and a temperature, impedance, pressure interface module. The central ablation control system unit 210 can control the operation of the RF system and/or the cryo system to operate the RF-cryo system 200 in the RF mode and/or the cryo mode.

For example, the central ablation control system unit 210 can control the elements that deliver the cryogen to the RF-cryo probe 202 when the RF-cryo system 200 operates in a cryo mode. The control system unit 210 can interface with the cryo interface module 214, the ablation sensing, monitoring, pump, heating power, pain control unit 218 to operate a pump that may be connected to a liquid or gas freezing material (e.g., cryogen). The control system unit 210 can operate the pump, heaters, valves, and/or other elements of the cryo system to deliver the cryogen at a desired temperature, pressure, flow rate, pulse rate, frequency and the like to cause the formation of an iceball at the distal end of the probe 202.

The central ablation control system unit 210 can also control the elements that deliver suitable power to cause the RF emitter in the probe 202 to heat the probe and/or the tissue at or near the distal end of the probe 202. For example, the control system unit 210 can send or receive signal or current via the RF frequency power and lead control 212 and the ablation sensing, monitoring, pump, heating power, pain control unit 218 to send a power signal to the RF emitter in the probe 202. The power signal may have a predetermined duty cycle, frequency, pulse width, power profile, power level, and the like to cause a desired amount of heating to be occur at the distal end of the probe 202.

The control system unit 210 and/or the ablation sensing, monitoring unit 218 may interact with one or more electrical leads, impedance sensors, temperature sensors, pressure sensors, or other sensors located on the probe 202 to collect various measurements regarding the conditions of the patient and/or operating parameters of the combination RF-cryo system 200. The measurement data from the previously described sensors can be routed via the data bus 224 to the RF-cryo computing device 206 for processing, storage or the like. In some instances, the measurement data can be compared to predetermined operating parameters ranges, operating parameter limits or the like and the RF-cryo computing device can adjust the operating parameters of the combination RF-cryo system 200 to achieve a desired operating condition during treatment.

While not shown, the RF-cryo computing device 206 may be coupled either wirelessly or via wired connections to other data sources, data repositories, or the like. The RF-cryo computing device 206 may obtain treatment plans and/or preferred operating conditions for a particular patient, treatment procedure, or the like. The RF-cryo computing device 206 may also store measurement data in a local or remote database that may be collected during a procedure or treatment for further use and/or processing.

The housing 240 of the RF-cryo controller 204 may also include a speaker 226 and/or a door control 238. The speaker 226 may be coupled to the data bus 224 can may be controlled to provide audible alerts or messages regarding the operation of the RF-cryo system 200. The door control 238 may operate to all connection of the RF-cryo probe 202. The door control 238 may also allow a door to be opened by a user for repair or maintenance. The door control 238 may include a door sensor to provide a signal when the door is in an open or closed position. The door control 238 may also include a light emitting diode (LED) that can be controlled to provide indicators and/or alerts to a user of the operating conditions of the RF-cryo controller 204.

Figure 3:
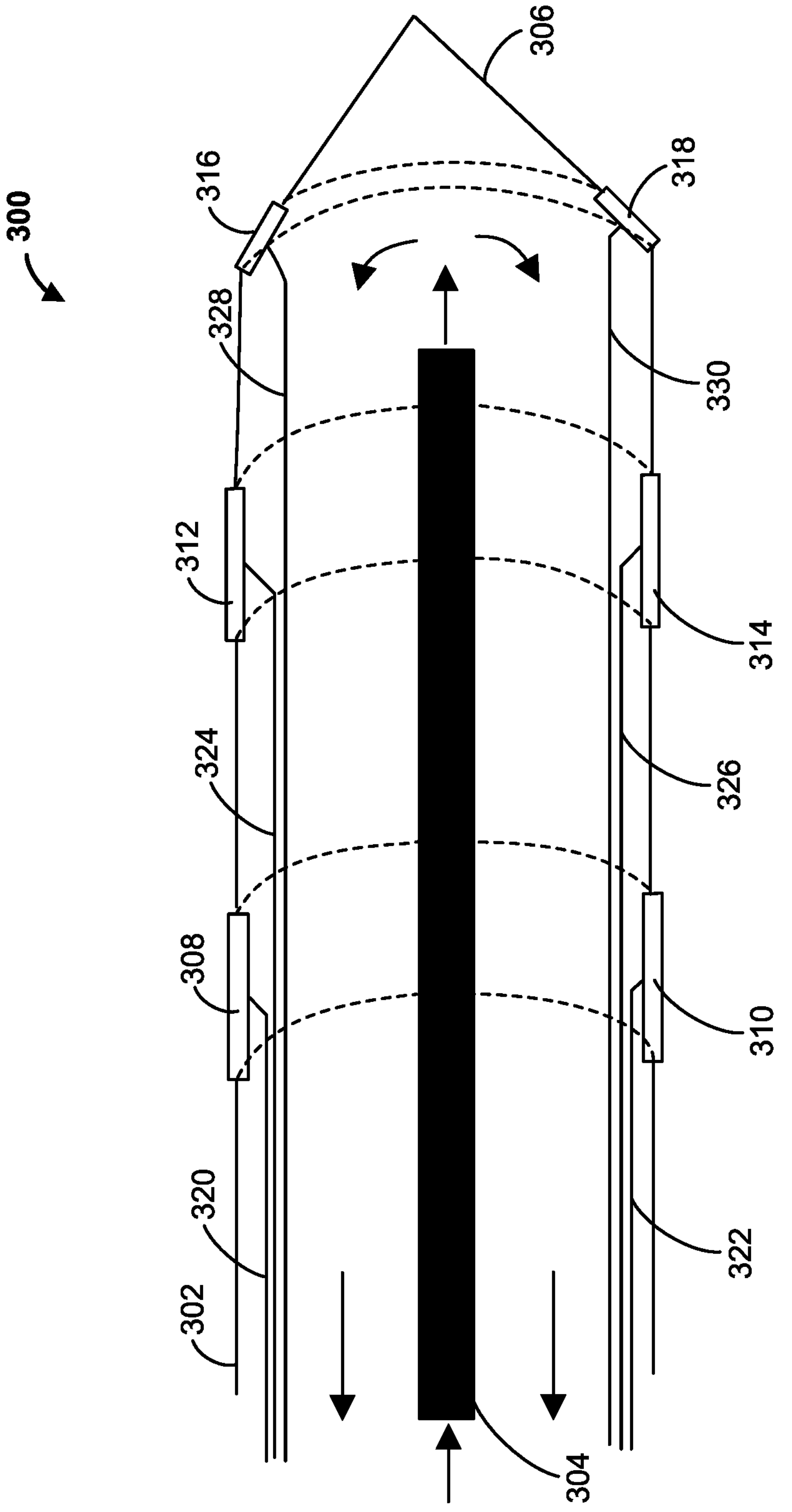
FIG. 3 is a side view of an example RF-Cryo probe in accordance with some embodiments of the present disclosure.

Referring now to FIG. 3, an example RF-cryo probe 300 is shown. The probe 300 can be operated in a RF mode and in a cryo mode. The probe 300 can include a cryogen conduit 304 through which cryogen can be moved from a dewar or other cryogen source to a distal end 306 of the probe 300. The cryogen may move in the probe 300 along a cryogen path that includes an inflow path such as the conduit 304 and an outflow path defined by an internal surface of the shell 302 and an external surface of the conduit 304. A pump may be used to move the cryogen from the cryogen source through the cryogen path. The probe 202 may employ various suitable cooling methodologies including Joules-Thompson cooling, critical cooling, and/or near-critical cooling processes. Any suitable liquid or gaseous cryogen can be used such as nitrogen, argon, or oxygen.

The probe 300 also includes one or more RF emitters that can deliver RF energy the target tissue. In this example, the probe 300 includes a first RF pad 308, a second RF pad 310, a third RF pad 312, a fourth RF pad 314, a fifth RF pad 316, and a sixth RF pad 318. Each of the RF pads can be positioned at different locations on shell 302 of the probe 300. In this example, the first and second RF pads, 308, 310 are positioned a first axial location away from the distal end 306. While the first and second RF pads 308, 310 are positioned at the same axial location, each of the first pad 308 and the second pad 310 are positioned at different circumferential locations around the exterior surface of the probe 300. The third and fourth RF pads 312, 314 are positioned at a different axial location closer to the distal end 306. The fifth and sixth RF pads are positioned closest to the distal end 306. The example probe 300 shows but one example layout of the RF pads on the probe. In other examples, the probe 300 may include more than six RF pads or less than six RF pads. In addition, the RF pads may be positioned in other locations to provide functionality as may be desired.

Each of the RF pads may be connected to the RF system that can provide RF energy and/or deliver a measurement to the RF-cryo controller. The first RF pad may be coupled to the RF-cryo controller via a first lead 320. The second RF pad 310 may be coupled to the RF-cryo controller via a second lead 322. The third RF pad 312 may be coupled to the RF-cryo controller via a third lead 324. The fourth RF pad 314 may be coupled to the RF-cryo controller via a fourth lead 326. The fifth RF pad 316 may be coupled to the RF-cryo controller via a fifth lead 328. The sixth RF pad 318 may be coupled to the RF-cryo controller via a sixth lead 330. Each of the leads 320, 322, 324, 326, 328, 330 may be a length of wire or other conductive path and may extend through or inside the shell 302. In other examples, the leads may be embedded in the shell 302 or be secured or embedded in a layer on the outside or inside of the shell 302.

In some examples, the pads and/or the leads can be added to the shell 302 in a separate layer that can be added to the external surface of the probe 300. In other examples, the probe 300 may be created using 3D printing processes and/or additive manufacturing processes. In still other examples, the pads and/or the leads can be part of a flexible circuit that is added or secured to the external surface of the probe 300. Probes with flexible circuits are further described in U.S. Patent Appl. No. 17/845,647 titled Ablation Probes Including Flexible Circuits for Heating and Sensing filed on the same day as the present application to Varian Medical Systems, Inc. The contents of the aforementioned application is incorporated herein in its entirety.

Each of the pads 308, 310, 312, 314, 316, 318 may be operated independently from one another to deliver the RF energy to the tissue as may be desired to cause heating of a local area. The pads can be controlled, for example, by the RF-cryo controller 104, 204 previously described. In other examples, each of the pads 308, 310, 312, 314, 326, 318 may be configured to measure an individual impedance or other measurement from a local area.

The RF energy that is delivered to the pads 308, 310, 312, 314, 316, 318 by the leads 320, 322, 324, 326, 328, 330, respectively can have various characteristics and can be independently controlled as may be desired. For example, the RF energy may have a predetermined energy level, current, frequency, duty cycle, amplitude, pulse width, or the like. The characteristics of the RF energy delivered to the pads may be based on the type of tissue, the desired heating level, the desired pain relief, the size of the target tissue, a desired ablation zone, and the like. The predetermined characteristics of the RF energy may be determined, for example, using experimental data and/or historical treatment data to develop algorithms, treatment models, and the like.

Figure 4:
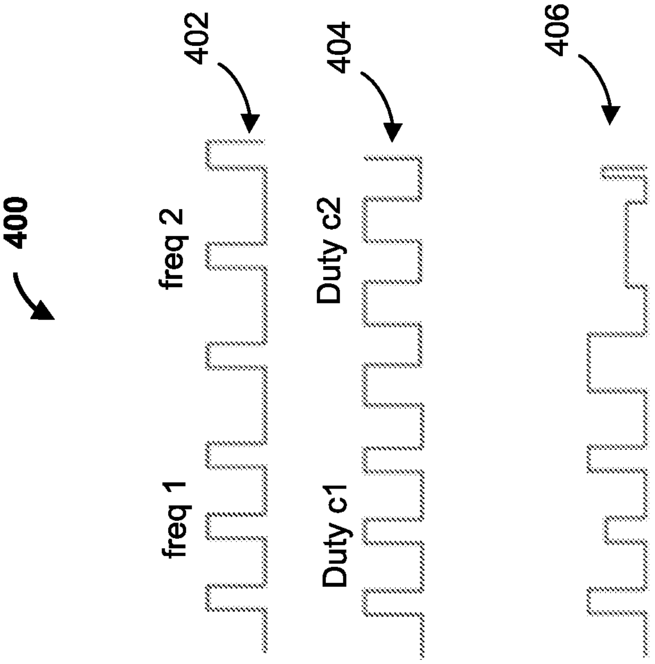
FIG. 4 is an illustration of various example duty cycles that can be used by the RF-Cryo ablation systems of the present disclosure.
Figure 5:
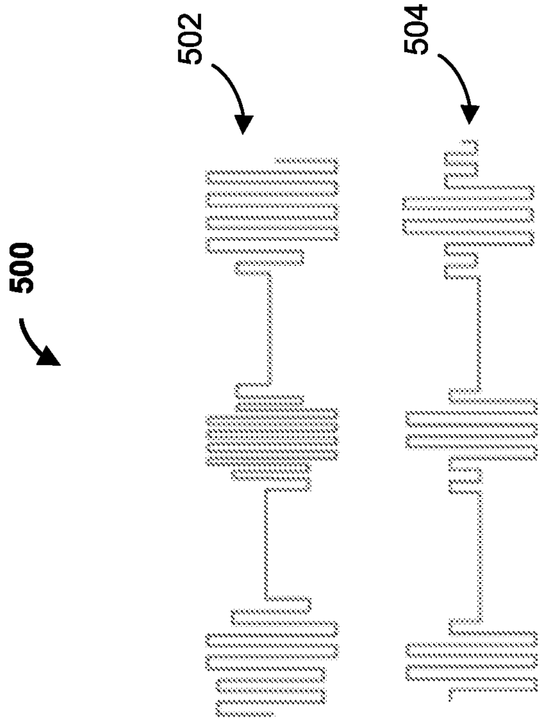
FIG. 5 is an illustration of various RF signals that can be used the RF-Cryo ablation systems of the present disclosure.

Referring now to FIGS. 4 and 5, different control examples are shown that may be used in connection with the probes of the present disclosure. The control examples may be used in connection with the probe 300 previously described. It should be appreciated, however, that the control examples can be used with variations of the probe 300 and other example probes described herein.

As shown in FIG. 4, one example control may use RF frequency control. The RF-cryo controller 104, 204 may control and/or provide RF energy to the pads/electrodes of the probe 300 using various frequency and/or duty cycles. In one example profile 402, the frequency of the RF signal may be varied according to clinical, heating, and/or pain relief needs for a particular treatment. In another example 404, a duty cycle of the RF signal may be varied according to clinical, heating, and/or pain relief needs for a particular treatment. In still another example 406, amplitude modulation of the RF signal many be used and varied according to clinical, heating, and/or pain relief needs for a particular treatment. Any of the these or other control of the RF signal may be used to deliver a common RF signal to one or more of the pads/electrodes of the probe 300. Different RF signals that use a combination of the control examples 400 can be used to deliver different RF signals to different pads/electrodes of the probe 300 as well.

Turning now to FIG. 5, example control 500 is shown. In this example RF signal profiles 502, 504 may be delivered to one or more of the pads/electrodes of probe 300. In some examples, the same RF signal profile may be delivered to a group of pads/electrodes. The RF signal profile 502 may be delivered to pads/electrodes 308, 312. The RF signal profile 504 may be delivered to pads/electrodes 310, 314. The delivery of different RF signal profiles to different pads/electrodes and/or to different groups of pads/electrodes may be desirable due to differences in the tissue that may be located at a particular region of the probe 300. The probe 300 may also be located near to a healthy tissue on one side or at one region of the probe 300. The RF signal that is delivered to a particular pad/electrode may, therefore, be different at the location near the healthy tissue. In still other examples, the various pads/electrodes can be performing differing functions during a common treatment. For example, some pads/electrodes may be heating a tissue location. Other pads/electrodes may be providing pain relief. Still other pads/electrodes may be performing a coagulation process at another tissue location. The various RF profiles may be used to perform these different functions and for other functions as described herein or known to one of skill in the art.

Figure 6:
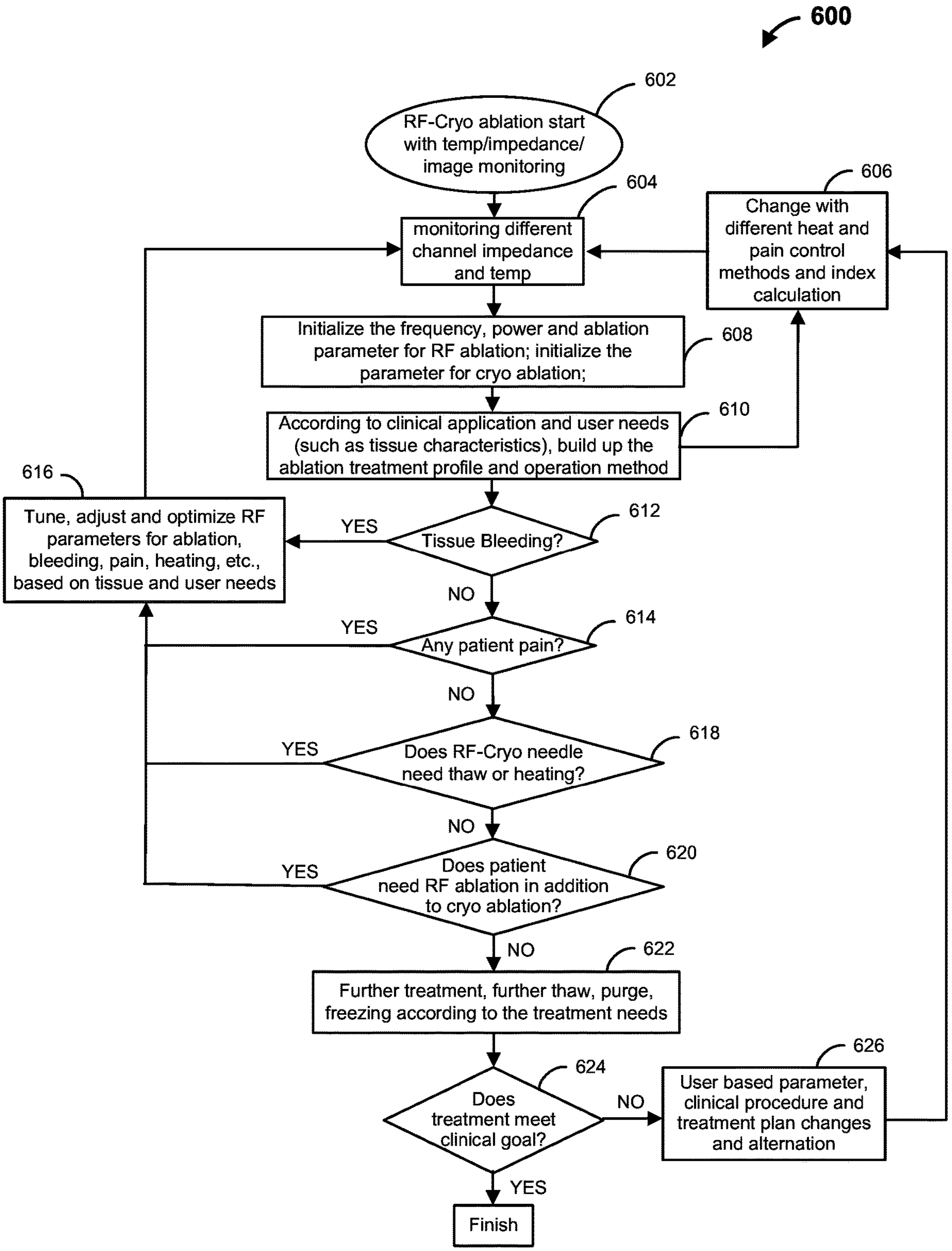
FIG. 6 is a flow chart illustrating an example method of performing an ablation treatment in accordance with some embodiments of the present disclosure.

Referring now to FIG. 6, an example method 600 of performing a treatment is shown. The method 600 may be performed using one of the combination RF-cryo systems of the present disclosure, including combination RF-cryo system 100, 200. While particular combination RF-cryo systems are used to aid in the description of the method 600, it should be appreciated that other RF-cryo systems can also be used and the method is not limited to particular system, probe, or apparatus.

The method 600 may begin at step 602. At step 602, a combination RF-cryo treatment may start with the collection of measurement data. The measurement data may include temperature, impedance, image, pressure, flow and other monitoring of conditions of the patient and of the combination RF-cryo system. At step 604, impedance and temperature data collection may occur. The impedance and temperature data may be collected from the probe 300. The probe 300 may include pads and/or sensors that can collect temperature and impedance measurements. The measurement data can be sent to or obtained by the RF-cryo controller 104, 204.

At step 608, the RF-cryo system 100, 200 can be initialized with predetermined or initial operating parameters. Such parameters may be determined as part of a treatment plan that can be obtained by the RF-cryo controller 104, 204. The various parameters such as the characteristics of the RF signal, temperatures of a cryogen, pressure of a cryogen, flow rate of the cryogen, and the like may be included in the initial operating parameters.

At step 610, a user may build or configure the treatment plan. The user may interface with the RF-cryo controller 104, 204 using a user interface on the RF-cryo computing device 106, 206, for example. The user may modify, change, or adjust the treatment plan and/or may modify the operating parameters of the RF-cryo system 100, 200 as may be desired. In some instances, the treatment may be initiated and move to step 612. In other instances, the method 600 may proceed to step 606.

The method 600 may move to step 606 when the circumstances of particular treatment such as the tissue conditions, the conditions of the patient (e.g., pain and health), or other conditions indicate that the treatment plan needs further modification or revision. In such instances, the treatment plan can be revised and input to the RF-cryo controller 104, 204. Such changes may include different heat and/or pain control methods and/or other treatment modifications. According to clinical application and user needs, e.g. the tissue location, impedance, blood flow, temperature, tissue material (muscle, fat, bone, etc.), different ablation parameters may be utilized, such as Microwave frequency, cryo ablation pressure/duration, on/off time, duty cycle, etc., can be automatically and adaptively adjusted and manipulated according to user feeling (such as comfortness index) and doctor feedback (operation time, temp estimation, ice ball size estimation, pain level, etc.). Additionally, some of the parameters' control may be based on the calculation index, such as impedance changes, temperature change rate, and patient pain level changes, etc. After step 606, the method 600 can return to step 604 and proceed as described.

If the method proceeds to step 612 after step 610, the treatment may be initiated and a cryo or RF cycle may be initiated. At step 612, the RF-cryo controller 104, 204 and/or the RF-cryo computing device 106, 206 may determine whether tissue bleeding is occurring. Such a determination may be made, for example, using the impedance measurements obtained from the probe 300. A bleeding condition can be determined, for example, by comparing the impedance measurement to a predetermined bleeding impedance range. Bleeding conditions may also be determined by measuring a change in impedance and comparing the change in impedance to predetermined range or threshold. If tissue bleeding is observed, the method 600 can move to step 616. If no tissue bleeding is observed, the method 600 can move to step 614.

At step 616, the RF-cryo controller 104, 204 may adjust the operating parameters of the RF-cryo system 100, 200 to take remedial measures to address the bleeding condition. For example, the RF-cryo controller may adjust and/or send a RF signal to a RF emitter (e.g., RF pad or electrode) in the region of the detected bleeding to initiate a coagulation cycle. Such a cycle may heat the region in which bleeding is detected to increase coagulation in the region. Such a corrective action or adjustment may be performed locally using one or more of the RF pads of the probe 300. After step 616, the method 600 may return to step 604 to reperform the steps of method 600 as previously described. In this manner, the RF-cryo controller 104, 204 can perform actions to address changes, such as bleeding conditions, that may occur during the course of treatment.

At step 614, the RF-cryo controller 104, 204 and/or the RF-cryo computing device 106, 206 may determine whether a pain condition is observed with the patient. The RF-cryo controller 104, 204 may determine if a pain condition is present. For patient pain level and comfort level, different parameters and/or indexes may be used, determined or developed based on the clinical needs and medical professional estimation. Patient feedback for pain level may be used during a procedure to adjust the operation parameters, such as microwave power, frequency and temperature. In addition, various measurements and/or indicators may be used to determine pain level or a pain condition. Such indicators may include patient heart rate, muscle response, facial reflection, breath rate, etc. These indicators and/or other vital signs and patient response mechanical and bio-electrical signals can also be utilized for patient pain and comfortness level determination and quantification. Such measurements, indicators, and signals may be compared to predetermined levels, ranges or other thresholds to determine if a pain condition is present. If a pain condition is detected, the method 600 may move to step 616. If no pain condition is present, the method 600 may move to step 618.

At step 616, the RF-cryo controller 104, 204 may make changes, modification or other revisions to the operating conditions of the RF-cryo system 100, 200 to address the pain condition. For example, the RF-cryo controller 104, 204 may cause a RF signal to be delivered to the target tissue via one or more of the RF pads/electrodes on the probe 300. The RF signal may be suitable to alleviate and/or reduce the pain condition that is detected. After such change, adjustment, and/or remedial action is taken by the RF-cryo controller at step 616, the method 600 may return to step 604 to reperform the steps of method 600 previously described. Thus, the RF-cryo system 100, 200 can also take action to alleviate pain conditions in addition to the other functionality described.

At step 618, the RF-cryo controller 104, 204 may determine whether the needle or probe requires a thaw or heating cycle. Such a thaw or heating cycle may be performed after a freezing cycle, in some example treatments. The thaw or heating cycle can be performed to allow for the probe 300 to be removed from the iceball and/or frozen tissue that may be formed during a freezing cycle. In other examples, a heating cycle may be performed to return frozen tissue to a normal body temperature. Such a heating cycle may be needed if a body structure needs to be repaired using a cement or other repair substance as previously described. In yet other examples, a heating or thaw cycle may be performed for coagulation or to denature proteins at the probe site to prevent and/or reduce the likelihood of contamination of the treatment site. The RF-cryo controller 104, 204 may determine whether a thaw or heating cycle is to be performed by retrieving such information from a treatment plan. In other examples, the RF-cryo controller 104, 204 may receive such information from an input device. If a thaw or heating cycle is needed, the method 600 may proceed to step 616. If no thaw or heating cycle is needed, the method 600 may proceed to step 620.

At step 616, the RF-cryo controller 104, 204 may adjust the operating parameters of the RF-cryo system 100 to perform the thaw or heating cycle that is needed. The RF-cryo controller 104, 204 may initiate the deliver of a suitable RF signal to one or more corresponding RF pads/electrodes to perform the thaw or heating cycle. After such action is taken, the method 600 can return to step 604 to reperform the steps of method 600 previously described.

At step 620, the RF-cryo controller 104, 204 may determine whether RF ablation is needed in addition to cryo ablation. The treatment plan may detail whether such an RF ablation cycle is to be performed. The RF-cryo controller 104, 204 and/or the RF-cryo computing device 106, 206 may retrieve such information. The information may be retrieved from a database or may be retrieved from an input device in which a medical professional may enter or supply such information. If RF ablation is needed or desired, the method 600 may proceed to step 616. IF no RF ablation is needed or desired, the method 600 may proceed to step 622.

At step 616, the RF-cryo controller 104, 204 may initiate the RF ablation by changing, adjusting, or initiating operation of one or more elements of the RF-cryo system 100, 200. For example, the RF-cryo controller 104, 204 may cause a suitable RF signal to be sent to the RF pad/electrode to initiate RF ablation. After step 616, the method 600 may return to step 604 to reperform the step s of method 600 as previously described.

At step 622, further treatment, further thaw, purge or freezing cycles may be performed. The treatment plan, for example, may detail repeated freezing cycles and/or repeated heating cycles. The particular needs and conditions of the tissue and the patient can dictate the details of the treatment plan.

At step 624, the RF-cryo controller 104, 204 may determine whether the treatment meets the clinical goal. The RF-cryo controller 104, 204 may make this determination by comparing measurement data to anticipated measurement data. Imaging data may also be collected that may measure aspects of the treatment such as location of the probe 300, size and location of an iceball, and/or other aspects of the treatment. This information can be used to determine whether the treatment meets the clinical goal. If the clinical goal has been met, the method can end. If the clinical goal has not been met, the method may proceed to step 626.

At step 626, the treatment plan, operating parameters, and/or clinical procedure can be changed. The RF-cryo controller 104, 204 and/or the RF-cryo computing device 106, 206 may recommend such changes and present such recommendations to a user or medical professional. The method may move to step 606 after step 626 to implement such recommendations and/or changes to the treatment plan, operating parameters, and/or the clinical treatment. The method may then return to step 604 to reperform the steps as previously described except with the changes determined at step 626.

Figure 7:
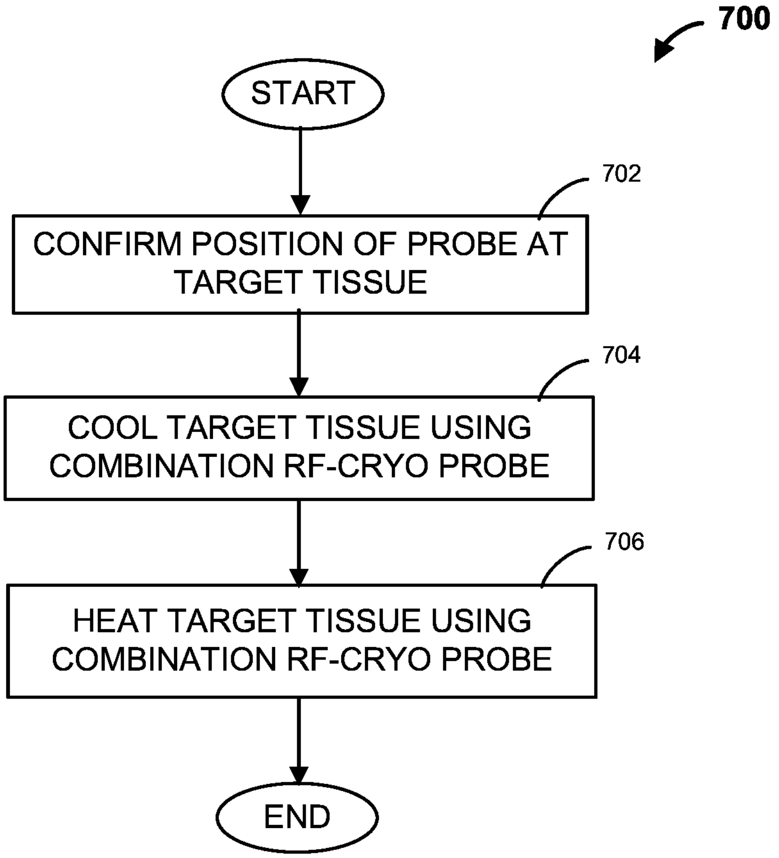
FIG. 7 is a flow chart illustrating another example method of performing an ablation treatment in accordance with some embodiments of the present disclosure.

Referring now to FIG. 7, another example method 700 of performing a combination RF-cryo treatment is shown. The method 700 may be performed, for example, using the various systems and probes described in the present disclosure such as RF-cryo system 100, 200 and probe 300. It should be appreciated, however, that other systems and devices can also be used.

The method 700 begins at step 702. At step 702, the RF-cryo controller 104, 204 and/or the RF-cryo computing device 106, 206 may confirm a position of the probe 300 at the target tissue. The position of the probe 300 may be confirmed using imaging device that may provide imaging data to the RF-cryo controller 104, 204 and/or the RF-cryo computing device 106, 206. In a desired position, the probe 300 may inserted into or near to a target tissue such as a tumor, lesion, or other abnormal tissue.

At step 704, the tissue may be cooled using the combination RF-cryo probe 300. The RF-cryo controller 104, 204 and/or the RF-cryo computing device 106, 206 may initiate the flow of cryogen from a cryogen source to the probe 300. This flow of cryogen may begin to cool and freeze the target tissue at or near the distal end of the probe 300. An iceball may begin to form at the distal end of the probe 300. The RF-cryo controller 104, 204 and/or the RF-cryo computing device 106, 206 may initiate the flow of cryogen using predetermined operating characteristics of the RF-cryo system 100, 200 such as a temperature, pressure, flow rate, pulse width, or characteristic of the cryogen flow.

At step 706, the RF-cryo controller 104, 204 and/or the RF-cryo computing device 106, 206 may then heat the target tissue and/or the probe 300 using an RF emitter in the combination RF-cryo probe 300 such as the RF pads previously described. In other examples, the tissue may be heated using a microwave antenna included in the probe 300. The RF-cryo controller 104, 204 and/or the RF-cryo computing device 106, 206 may heat the target tissue in a desired location relative to the probe 300 and in a desired manner according to the desired result. The heating at step 706 may be performed to thaw the iceball that has formed at the probe for removal of the probe 300. The heating at step 706 may be performed to return the target tissue or an adjacent body structure such as bone to a normal body temperature so that a structural cement or other repair procedure can be performed. The heating at step 706 may be performed to cause coagulation of bleeding condition. The heating at step 706 may also be performed to denature proteins at the site of the probe 300 if, for example, the probe 300 is repositioned in the tissue.

As previously described, the RF-cryo controller 104, 204 and/or the RF-cryo computing device 106, 206 may cause various RF signals to be delivered to one or more RF emitters in the probe 300 and/or to one or more groups of RF emitters in the probes. In this manner, the heating cycle at step 706 may have different heating conditions at different locations on the probe 300.

The method 700 and/or various steps of the method 700 may be repeated to allow various treatments to be performed that may include multiple freezing ablation cycles, multiple RF ablation cycles, coagulation treatments, pain relief treatments, denaturing processes, and the like. In addition, the method 700 may be performed using a single combination RF-cryo probe such as probe 300. This allows the multiple treatment cycles to be performed during a common treatment. This reduces the amount of procedures that need to be performed on a patient and reduces the impact of the treatment on health tissues of the patient.

Figure 8:
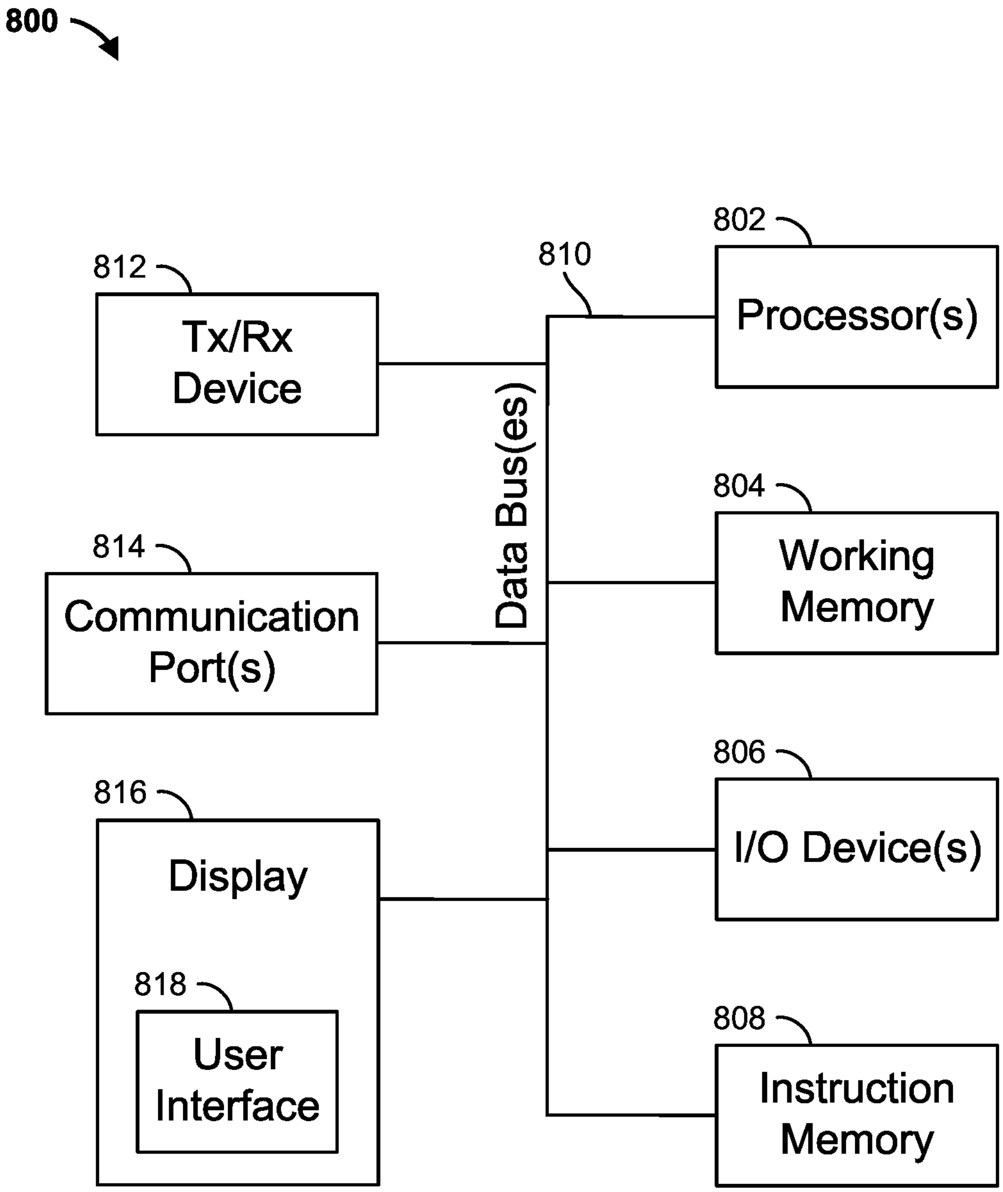
FIG. 8 is a diagram illustrating an example computing device that can be used in one or more cryoablation systems of the present disclosure.

Referring now to FIG. 8, an example computing device 800 is shown. The combination RF-cryo ablation system 100, 200 may include one or more computing devices 800. For example, the RF-cryo computing device 106, 206 may have the elements shown in FIG. 8. The methods of the present disclosure, such as method 700, may be performed, or steps of such methods may be performed, by a computing device 800.

As shown, the computing device 800 may include one or more processors 802, working memory 804, one or more input/output devices 806, instruction memory 808, a transceiver 812, one or more communication ports 814, and a display 816, all operatively coupled to one or more data buses 810. Data buses 810 allow for communication among the various devices. Data buses 810 can include wired, or wireless, communication channels.

Processors 802 can include one or more distinct processors, each having one or more cores. Each of the distinct processors can have the same or different structure. Processors 802 can include one or more central processing units (CPUs), one or more graphics processing units (GPUs), application specific integrated circuits (ASICs), digital signal processors (DSPs), and the like.

Processors 802 can be configured to perform a certain function or operation by executing code, stored on instruction memory 808, embodying the function or operation. For example, processors 802 can be configured to perform one or more of any function, step, method, or operation disclosed herein.

Instruction memory 808 can store instructions that can be accessed (e.g., read) and executed by processors 802. For example, instruction memory 808 can be a non-transitory, computer-readable storage medium such as a read-only memory (ROM), an electrically erasable programmable read-only memory (EEPROM), flash memory, a removable disk, CD-ROM, any non-volatile memory, or any other suitable memory.

Processors 802 can store data to, and read data from, working memory 804. For example, processors 802 can store a working set of instructions to working memory 804, such as instructions loaded from instruction memory 808. Processors 802 can also use working memory 804 to store dynamic data created during the operation of RF-cryo computing device 106. Working memory 804 can be a random access memory (RAM) such as a static random access memory (SRAM) or dynamic random access memory (DRAM), or any other suitable memory.

Input-output devices 806 can include any suitable device that allows for data input or output. For example, input-output devices 806 can include one or more of a keyboard, a touchpad, a mouse, a stylus, a touchscreen, a physical button, a speaker, a microphone, or any other suitable input or output device.

Communication port(s) 814 can include, for example, a serial port such as a universal asynchronous receiver/transmitter (UART) connection, a Universal Serial Bus (USB) connection, or any other suitable communication port or connection. In some examples, communication port(s) 814 allows for the programming of executable instructions in instruction memory 808. In some examples, communication port(s) 814 allow for the transfer (e.g., uploading or downloading) of data, such as measurement data and the like.

Display 816 can display a user interface 818. User interfaces 818 can enable user interaction with the RF-cryo computing device 106. For example, user interface 818 can be a user interface that allows an operator to interact, communicate, control and/or modify different messages, settings, or features that may be presented or otherwise displayed to a user. The user interface 818 can include a slider bar, dialogue box, or other input field that allows the user to control, communicate or modify a setting, limitation or input that is used in a cryoablation treatment. In addition, the user interface 818 can include one or more input fields or controls that allow a user to modify or control optional features or customizable aspects of the RF-cryo computing device 106 and/or the operating parameters of the combination RF-cryo system 100. In some examples, a user can interact with user interface 818 by engaging input-output devices 806. In some examples, display 816 can be a touchscreen, where user interface 818 is displayed on the touchscreen. In other examples, display 816 can be a computer display that can be interacted with using a mouse or keyboard.

Transceiver 812 allows for communication with a network. In some examples, transceiver 812 is selected based on the type of communication network RF-cryo computing device 106 will be operating in. Processor(s) 802 is operable to receive data from, or send data to, a network, such as wired or wireless network that couples the elements of the cryoablation system 100.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A probe for performing an ablation treatment comprising:

a shell defining an outer surface;

a cooling path positioned inside the shell comprising an inflow path and a return path for a cryogen, wherein the cooling path comprises a supply conduit, the inner surface of the supply conduit defining the inflow path, and the outer surface of the supply conduit and an inner surface of the shell defining the outflow path; and a plurality of radio frequency (RF) pads each positioned at a different location on the shell, wherein the plurality of radio frequency (RF) pads comprise a first RF pad and a second RF pad positioned at a same axial location relative to a distal end of the shell and at a different circumferential location around the outer surface of the shell, wherein the plurality of RF pads comprise a third RF pad positioned on a beveled surface at the distal end of the shell, and wherein the plurality of RF pads are configured to deliver RF energy, and wherein the RF energy is adjustable to thaw ice, perform coagulation, and alleviate pain.

2. The probe of claim 1, wherein the cooling path is positioned radially inward of the shell and is configured to move liquid or gaseous nitrogen through the probe.

3. The probe of claim 1, wherein the plurality of radio frequency (RF) pads comprises a third RF pad positioned at a first axial location relative to the distal end of the shell and a fourth RF pad positioned at a second axial location relative to the distal end of the shell that is different than the first axial location, the third RF pad positioned at a different circumferential location than the fourth RF pad.

4. The probe of claim 1, wherein the plurality of radio frequency (RF) pads comprises a microwave antenna.

5. A system for performing an ablation treatment comprising:

the probe of claim 1; and a RF-cryo controller configured to control operating characteristics of the cryogen and characteristics of a radio frequency signal provided to the plurality of radio frequency (RF) pads.

6. The system of claim 5, wherein the RF-cryo controller comprises at least one RF-cryo computing device and a data bus and is configured to independently control each radio frequency (RF) pad of the plurality of radio frequency (RF) pads.

7. The system of claim 5, wherein the RF-cryo controller is positioned in a housing comprising one or more connectors for connection of the probe.

8. The system of claim 5, wherein the RF-cryo controller is further configured to deliver a first radio frequency (RF) signal to the first radio frequency (RF) pad of the plurality of radio frequency (RF) pads and a second radio frequency (RF) signal to the second radio frequency (RF) pad of the plurality of radio frequency (RF) pads, the first radio frequency (RF) signal being different from the second radio frequency signal (RF).

9. The system of claim 5, comprising a plurality of leads coupling the RF-cryo controller to the plurality of radio frequency (RF) pads, wherein each one of the plurality of leads can deliver the RF energy to a corresponding one of the plurality of RF pads.

10. A method comprising:

cooling a target tissue by moving a cryogen through a shell of a probe; and heating the target tissue by emitting radio frequency (RF) energy from at least one of a plurality of radio frequency (RF) pads positioned on the shell of the probe, wherein the plurality of radio frequency (RF) pads comprise a first RF pad and a second RF pad positioned at a same axial location relative to a distal end of the shell and at a different circumferential location around the outer surface of the shell, wherein the plurality of RF pads comprise a third RF pad positioned on a beveled surface at the distal end of the shell, and wherein the radio frequency (RF) energy is adjustable to thaw ice, perform coagulation, and alleviate pain.

11. The method of claim 10, wherein the steps of cooling the target tissue and heating the target tissue are performed during a common treatment.

12. The method of claim 10, wherein the step of cooling the target tissue comprises forming an iceball at the target tissue, and wherein the step of heating the target tissue by emitting radio frequency (RF) energy comprises delivering a first radio frequency (RF) signal to the first radio frequency (RF) pad of the plurality of radio frequency (RF) pads and delivering a second radio frequency (RF) signal to the second radio frequency (RF) pad of the plurality of radio frequency (RF) pads, the first radio frequency (RF) signal being different from the second radio frequency signal (RF).

13. The method of claim 10, wherein the cryogen comprises liquid or gaseous nitrogen.

14. The method of claim 10, wherein the plurality of radio frequency (RF) pads are positioned at different locations on the shell.

15. The method of claim 10, wherein the plurality of radio frequency (RF) pads comprises a microwave antenna.

16. The method of claim 10, wherein the step of heating the target tissue comprises performing a coagulation treatment.

17. The method of claim 10, wherein the step of heating the target tissue comprises denaturing proteins at or near the target tissue.

18. The method of claim 10, wherein the step of heating the target tissue comprises ablating the target tissue.

19. The method of claim 10, further comprising adding cement to a body structure when the temperature of the body structure is greater than a predetermined temperature, and wherein the method is performed during a common treatment.

* * * * *